United States Patent
Aronson et al.

(10) Patent No.: US 6,329,331 B1
(45) Date of Patent: *Dec. 11, 2001

(54) DETERGENT COMPOSITIONS

(75) Inventors: Michael Paul Aronson, Edgewater, NJ (US); Charles Rupert Brown, Bedford (GB); Robert James Chatfield; Peter Fairley, both of Bebington (GB); Ian Timothy Norton, Bedford (GB); Jason Richard Williams, Edgewater, NJ (US)

(73) Assignee: Unilever Home & Personal Care USA, division of Conopco, Inc., Greenwich, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/281,624

(22) Filed: Mar. 31, 1999

(30) Foreign Application Priority Data

Apr. 3, 1998 (GB) .................................... 9807269

(51) Int. Cl.[7] .............................. A61K 7/48; A61K 7/50; C11D 3/22; C11D 3/37

(52) U.S. Cl. ..................... 510/158; 510/130; 510/135; 510/151; 510/159; 510/438; 510/470; 510/475; 510/511; 510/537

(58) Field of Search ........................ 510/130, 135, 510/151, 158, 159, 438, 470, 475, 511, 535–7

(56) References Cited

U.S. PATENT DOCUMENTS

| | | |
|---|---|---|
| 5,089,269 | 2/1992 | Noda et al. . |
| 5,151,210 | 9/1992 | Steuri et al. ............... 252/174.017 |
| 5,286,405 | 2/1994 | Rennie et al. .............. 252/147.17 |
| 5,658,875 * | 8/1997 | Giesen et al. ............... 510/470 |
| 5,663,137 * | 9/1997 | Giesen et al. ............... 510/470 |
| 5,700,455 * | 12/1997 | Hinterwaldner et al. ........ 424/70.14 |
| 5,789,372 * | 8/1998 | Fabry ...................... 510/502 |
| 5,910,472 * | 6/1999 | Elliott et al. .............. 510/124 |
| 5,925,747 * | 7/1999 | Uphues et al. .............. 536/18.5 |

FOREIGN PATENT DOCUMENTS

| | | |
|---|---|---|
| 0271131 | 6/1988 | (EP) . |
| 0355908 | 2/1990 | (EP) . |
| 0432835 | 6/1991 | (EP) . |
| 0355908 | 2/1992 | (EP) . |
| 1461775 | 1/1977 | (GB) . |
| 2188060 | 9/1987 | (GB) . |
| 98/08601 | 3/1998 | (WO) . |
| 98/12290 | 3/1998 | (WO) . |

OTHER PUBLICATIONS

"Scraped Surface Heat Exchangers", Magnus Harrod—Food & Nutrition Press, Inc. (1987) pp. 1–63.

"Industrial Gums, Polysaccharides and their Derivatives", Whistler et al.—Academic Press, (1959), pp. 51–55.

"Food Gels", Peter Harris—Elsevier Applied Science 1990), pp. 78–119.

"Rheology & Fracture of Mixed i–and κ–Carrageenan Gels: Two–Step Gelation", Parker et al., Carbohydrate Polymers 20 (1993) pp. 253–262.

"A Kinetic Investigation of the Extent of Polymer Aggregation in Carrageenan and Furcellaran Gels", Oakenfull et al.—Chemistry and Industry, (1987), pp. 201–202.

International Search Report Application No. PCT/EP 99/01901 mailed Aug. 4, 1999.

* cited by examiner

Primary Examiner—Yogendra N. Gupta
Assistant Examiner—Brian P. Mruk
(74) Attorney, Agent, or Firm—Ronald A. Koatz (57) ABSTRACT

An aqueous detergent composition, which is in the form of a thickened, mobile fluid, comprising foaming detergent and a polymer or polymer mixture which is capable of forming a reversible gel, which polymer or mixture is present in the composition as a multiplicity of individual gel particles.

11 Claims, 2 Drawing Sheets

DETERGENT COMPOSITIONS

This invention relates to foaming detergent compositions which may be for use in personal washing, or in other applications.

A number of detergent products for personal washing are formulated as viscous liquids, creams or gels. Examples of such products are hair shampoos, shower gels and facial washes. Such products generally contain foaming surfactant which usually comprises at least 3 wt % of anionic surfactant, possibly accompanied by amphoteric, zwitterionic or nonionic surfactant. It is conventional for such products to contain one or more ingredients whose function is to increase the viscosity of the composition. Some other liquid detergent compositions are also required to contain foaming surfactant and to have a viscosity greater than that of water.

One possibility for enhancing the viscosity of a fluid composition is to incorporate a sufficient quantity of electrolyte together with a sufficient quantity of selected surfactant, so that the surfactant is present in a viscous phase, and thus increases the viscosity of the resulting composition.

It is also known to incorporate polymeric materials to enhance viscosity. One category of synthetic polymers used for this purpose are crosslinked polyacrylates, for instance those sold under the trade mark Carbopol. Natural polymers have also been used for this purpose, and in particular xanthan gum and its derivatives has been used. Personal washing products, especially shampoos, containing xanthan gum are described in for example U.S. Pat. No. 5,151,210 and EP-A-500423.

Detergent products containing other polymers have been described, for example in U.S. Pat. No. 5,286,405 and GB-A-2188060.

EP-A-271131 discloses a number of products intended for application to skin which are thickened with carrageenan so as to form gels. Many of these do not include surfactant. One product disclosed in this document is a cleansing composition, containing a low foaming nonionic surfactant.

A number of polymers of biological origin, when in aqueous solution, have the ability to form so-called reversible gels which melt when heated but revert to a gel when cooled down subsequently. One well known example of a polysaccharide which forms reversible gels is agar. An aqueous solution containing a small percentage of agar is a mobile liquid when hot, but when left to cool it forms a gel with sufficient rigidity to maintain its own shape. Other naturally occurring polymers which can form reversible gels are carrageenan, furcelleran, gellan and pectin.

The formation of gels by natural polysaccharides arises from interaction between the polymer molecules. Reversible gels generally display a melting temperature or temperature range, referred to as the gel point. This is the temperature at which, on slow heating, the gel is observed to melt as this interaction largely disappears. Thus, above the gel point, the hot solution of polymer is mobile. When it cools below its gel point, the interaction of polymer molecules enables them to form a continuous and branched network which extends throughout the sample. In contrast with the formation of a continuous, branched network, some other materials which thicken water do so through merely local, transient entanglement of molecules. A discussion of polysaccharide gels, including their range of mechanical properties, is found in "Gels and Gelling" by Allan H Clark which is Chapter 5 in Physical Chemistry of Foods, Schwartzberg and Hartel, editors; published by Marcel Dekker 1992. In some instances there is hysteresis and the melting and setting temperatures are not identical.

The melting temperature of a gel can suitably be measured by placing a steel ball, having a diameter of approximately 1 mm, on the surface of a sample which is fully set, then raising the temperature slowly e.g. in a programmable water bath. The gel melting point is the temperature at which the ball begins to sink through the sample. Apparatus to facilitate such determinations is available, for example a Physica AMV200 rolling ball viscometer from Anton Paar KG.

A reversible gel also displays a transition temperature at which, upon slow temperature increase, all ordering, be it of microscopical or macroscopical extent, has disappeared completely. This transition temperature (from order to disorder) can be measured by means of differential scanning calorimetry (DSC). The transition temperature of a reversible gel, as measured by DSC, usually approximately coincides with gel melting, observable visually.

Although xanthan gum can be incorporated as a thickener in aqueous compositions containing surfactant, the resulting products tend to have a stringy texture and a slimy feel. We have found that the gels formed on cooling of a number of other polymers of biological origin are incompatible with foaming surfactants. The surfactant makes the gel unstable and phase separation occurs on cooling or on subsequent storage.

EP-A-355908 teaches that polysaccharides which are capable of forming a reversible gel can be used to form viscous, yet mobile, fluid compositions by subjecting the composition to shear while gel formation takes place. The resulting compositions can be termed "shear gels". This document exemplifies a number of products, one of which is named a "cleanser gel" and includes a low foaming nonionic surfactant as an emulsifier.

We have now found that it is possible to form detergent compositions which are shear gels and which include foaming surfactant.

According to the present invention, there is provided an aqueous detergent composition, which has a thickened fluid form, containing foaming surfactant and a polymer or polymer mixture which is capable of forming a reversible gel in water, which polymer is present in the composition as a multiplicity of separate gel particles.

In the present specification, the expression "thickened fluid" is used to denote a composition with viscosity greater than that of water.

In order that the gel particles remain stable in the presence of surfactant, it will generally be desirable that the polymer or polymer mixture does not require polyvalent cations in order to form the precursor aggregates that are subsequently capable of intermolecular association leading to formation of a gel network. Consequently it is desirable that the polymer or mixture is capable of forming a reversible gel when dissolved at a sufficient concentration in hot distilled or demineralised water and allowed to cool to an ambient temperature of 20° C.

The composition may consist solely of a continuous aqueous phase and the gel particles therein. However, compositions thickened with gel particles, in accordance with this invention have been found to be very effective at suspending other materials and so a composition of this invention may incorporate suspended particles of a water-immiscible liquid (eg a water-immiscible oil) or of a solid other than polymer gel. The amount of such particles may lie in a range from 0.1 to 40% by weight, preferably 0.1 to 25% by weight, more preferably 0.5 to 20% by weight of the composition.

Compositions embodying this invention may be made with viscosities in a wide range. At one extreme, the compositions may be freely mobile, self-levelling and pourable, although thicker than water. On the other hand, they may be made as viscous liquids which can be squeezed from a collapsible container, and yet which are too viscous to pour, except very slowly.

They are shear-thinning, which can be a useful property, notably in personal washing compositions, because the user can perceive the product as thick and viscous, and yet find it easy to apply. An advantage of viscous shear gels, as compared to compositions thickened in some other way, is that they are better at retaining the shape which has been squeezed out.

If the compositions are heated to a temperature above the melting and transition temperatures, the individual gel particles will melt and will not reform as separate particles on cooling, but this will not be a problem in ordinary use, because reversible gels generally have melting temperatures well above normal room temperatures.

Viscosity of compositions embodying this invention can be measured using the same techniques as are used to measure viscosities of other thickened liquid compositions. One suitable apparatus is the Haake Rotoviscometer, another is the Carri-Med CSL 500 viscometer.

Many compositions of this invention will display a viscosity in a range from 0.1 Pa.s to 100,000 Pa.s at a shear rate of 10 sec$^{-1}$, measured at 20° C., more preferably a viscosity in the range 0.1 Pa.s to 20,000 Pa.s at a shear rate of 10 sec$^{-1}$, measured at 20° C., more preferably a viscosity in the range 0.1 Pa.s to 10,000 Pa.s at a shear rate of 10 sec$^{-1}$, measured at 20° C., more preferably a viscosity in the range 0.1 Pa.s to 1,000 Pa.s at a shear rate of 10 sec$^{-1}$, measured at 20° C.

One route for the preparation of the sheared gel particles required for this invention starts with the provision of an aqueous solution of the polymer or polymer mixture, at a temperature above the gel melting temperature (and probably also above its order to disorder transition temperature), then cooling the solution to a temperature below the gel setting temperature, while applying shear to the composition. Generally, the solution will be subjected to shear while cooling from 60° C. or above to 25° C. or less.

On a small scale, this may be carried out in a beaker with a mechanical stirrer in the beaker, providing vigorous stirring while the contents of the beaker are allowed to cool.

We prefer to carry out the preparation using a scraped surface heat exchanger, which may desirably be equipped to operate under a partial vacuum, to reduce the incorporation of air bubbles into the composition as gel formation takes place.

Another possibility for preparing the gel particles is to form a bulk quantity of the gel and then break this up into small particles, for instance by pumping it through a homogeniser.

The gel particles will typically be of a size which can be seen in a microscope. Usually their mean particle size will lie in a range from 0.1 to 250 μm, and often almost all particles will lie between particle sizes of 0.1 to 300 μm. Preferably the mean particle size is between 0.5 or 1 μm and 200 μm may lie in a range from 10 μm up to 200 μm.

An advantage of gel particles having this particle size, particularly in the context of cleansing compositions, is that the small particles of polymer may enhance cleansing by mechanically breaking up soil on the surface being cleaned. This may be particularly so in the case of topical compositions used for make up removal.

Generally it will be desirable to form the gel particles by cooling an aqueous solution of the gel-forming polymer or polymer mixture in the substantial absence of surfactant, and then add surfactant subsequently. An alternative approach is to incorporate surfactant into the aqueous composition before the step of cooling under shear. This is not possible for all gel-forming polymers. We have found that for many polymers gel formation is inhibited by the presence of surfactant, and yet gel particles which have already been formed remain stable if surfactant is added subsequently.

Thus in a second aspect, this invention provides a method of preparing a detergent composition as set forth above which comprises forming a hot, mobile aqueous solution of the polymer or polymer mixture, cooling the solution through its gel temperature, subjecting it to shear during or after cooling, and incorporating foam-forming surfactant possibly before but preferably after cooling through the gel temperature.

A laboratory-scale jacketed mixing vessel with a scraped surface, which we have used successfully is the TK Agi Homo mixer available from Tokushu Kika Kogyo Co Ltd, Japan.

Scraped surface heat exchangers and homogenisers are used in the commercial production of margarine and other spreadable foodstuffs and such apparatus may be used to produce compositions of this invention on a larger scale. A discussion of such heat exchangers is given by Harrod in Journal of Food Process Engineering 9 (1986) pages 1–62. Suppliers of such apparatus include Armfield Ltd, Ringwood, Hampshire, England, Contherm Corporation which is a division of the Alfa-Laval Group, USA and APV Projects (Crepaco) Ltd, Crawley, West Sussex, England.

After the formation of gel particles, the addition of foam-forming surfactant or other ingredients, probably as a liquid concentrate but optionally as a solid surfactant or solid and/or melted acid surfactant precursor, can be carried out using conventional mixing apparatus, operating at low shear. Possibly a scraped surface heat exchanger used to form the gel particles can also be used for a subsequent mixing operation, especially if run more slowly, so as to give lower shear. A mixing operation should not be allowed to heat the composition sufficiently to cause melting of the gel particles. If necessary, a composition containing gel particles should be cooled before and/or during any subsequent mixing operation.

In a highly preferred embodiment, compositions according to the invention may comprise relatively high levels of polyol materials, which polyols have been found to confer to the compositions various benefits. These may include benefits in terms of processing, but also benefits in the resultant topical compositions.

Materials and procedures useful in this invention will now be described in greater detail by way of example only, making reference to the accompanying drawings, wherein:

Figure 1:
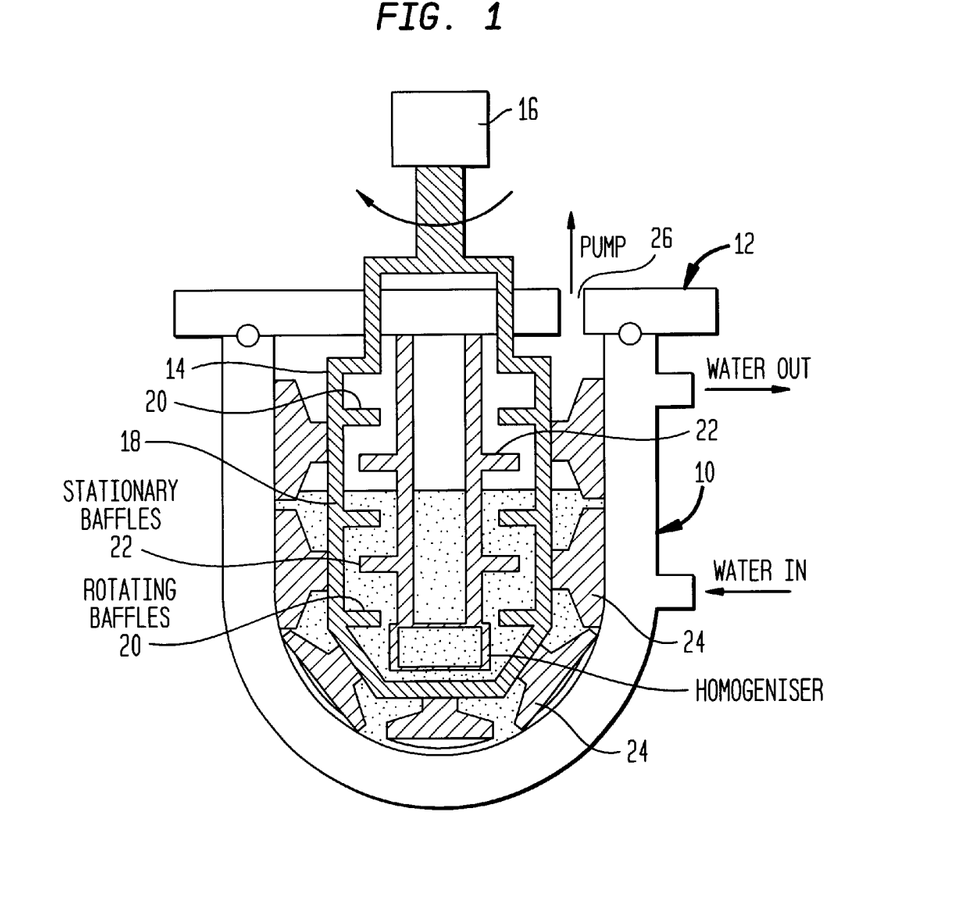
FIG. 1 is a cross-section of a mixer useful for preparing a shear gel particles on a batch basis, FIG. 2 diagrammatically illustrates apparatus for continuous preparation, FIG. 3 diagrammatically illustrates another form of apparatus used in Example 10 and FIG. 4 diagrammatically illustrates another form of apparatus used in Example 12.

The apparatus shown in FIG. 1 is a TK Agi homo mixer. It has a containing vessel 10 with inner and outer walls spaced apart to allow a coolant to be circulated through the space between them. The vessel has an upper closure 12. A rotor 14 within the vessel is extended through the upper closure 12 and connected to a drive motor 16. The rotor 14 surrounds a central fixed stator 18. Baffles 20,22 project from the rotor and stator respectively. When the rotor is turned the liquid within the vessel 10 is subjected to shear by the movement of the rotor 14 and its baffles 20 relative to the stator 18 and its baffles 22. In addition flaps 24 made of polytetrafluoroethylene projecting from the rotor 14 scrape the inner wall of the vessel 10. The upper closure 12 includes provision at 26 for connection to a vacuum pump. Gas tight seals are provided between the rotor 14 and the upper closure 12. Consequently vacuum can be applied to the interior of the vessel 10 through the connection 26.

In order to make a composition according the invention using this apparatus, an aqueous solution of the polymer, heated to above its gel temperature, is placed in the vessel. The upper closure 12 is then placed on the vessel and the contents of the vessel are cooled by circulation of coolant through the space between the vessel walls. At the same time the rotor is turned and vacuum is applied to the connection 26 so that cooling of the vessel contents takes place under conditions of shear, while suction through the air outlet 26 forming prevents formation of gas bubbles.

In consequence, as the contents of the vessel cool to below the gel point, a multiplicity of small gel particles are formed. Once the contents of the vessel have cooled below the gel temperature and these particles have formed, surfactant can be mixed with the vessel contents either by removing the upper closure and adding a liquid concentrate (or optionally a solid surfactant or solid and/or melted acid precursor) of the surfactant to the vessel 10, or by transferring the contents of the vessel 10 and also the surfactant, to a separate mixer.

Figure 2:
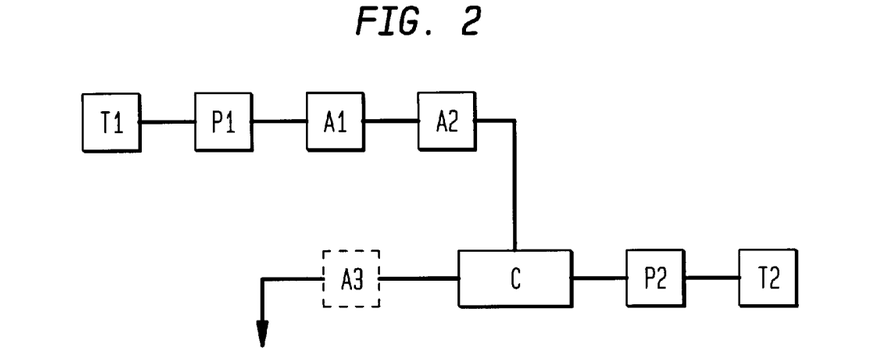

FIG. 2 illustrates a preferred form of apparatus consisting of several individual pieces of equipment connected together by pipework.

A hot aqueous solution of the polymer is prepared and held in a supply vessel T1. It is delivered from this by a suitable pump P1 to a scraped surface heat exchanger A1 which is in the form of a cylinder for through flow of the polymer solution and which is surrounded by a jacket for coolant. Within this heat exchanger is located a large diameter shaft fitted with scraper blades which are spring loaded to hold them against the interior surface of the cylindrical vessel wall. Rotation of this central shaft by a motor applies shear to the polymer solution as it passes through the heat exchanger A1.

As the polymer solution passes through the heat exchanger A1 it is cooled to below its gel temperature under conditions of shear and this leads to the formation of gel particles in continuous aqueous phase. The resulting composition passes on from heat exchanger A1 to a second heat exchanger A2 which is similar except that it operates at a lower speed. this is used to cool the composition further.

The composition then flows on to a mixer C which, like the units A1 and A2 performs heat exchange functions. However, within this C-unit there are stationary baffles projecting inwardly from the heat exchanger walls and a motor driven central, small diameter shaft which carries further baffles that project between the stationary baffles of the cylinder wall. There are no scapers in this device. Here, the composition is mixed with surfactant solution delivered from a supply vessel T2 by means of a suitable pump P2. The mixture leaving the high speed mixer C is a composition in accordance with the present invention. It may be convenient to cool it by passage through a further scraped surface heat exchanger A3 operating at low speed before the composition is delivered as finished product or packed in containers. The pumps P1 and P2 may conveniently be provided as separate channels of a proportioning piston pump, which is a convenient way to ensure that constant proportions are delivered from each of the tanks T1, T2.

Mixing apparatus, pumps and scraped surface heat exchangers used in apparatus as above can be of types which are customarily used in the production of margarine and other edible spreads. Another name for the scraped surface heat exchanger which provides for through flow of the material is a "votator". These pieces of apparatus may be manufactured in a range of sizes extending from small units which can fit on a laboratory bench to full scale production plant. Manufacturers of such apparatus include Armfield Ltd, Cantherm Corporation and APV Projects (Crepaco) Ltd mentioned above.

There are two generally preferred processes for preparing shear gel compositions according to the inventions using the above described equipment.

In the first, water, polymer, and optionally a polyol compound are added to a main mixer vessel (with or without a static homogenizer), and heated to 90° C. under vacuum. The mixture can then be cooled, under vacuum and using a high wall scraper speed, rapidly to 50° C., and then more slowly to 20° C.

The composition can then be subjected to a static homogenizer, whilst being warmed to 40° C. if need be, whilst surfactant or acid form of the surfactant is added to the top of the mixture. Alternatively, the surfactant can be added by dripping molten surfactant through the hopper contents, which can preferably be under vacuum and high shear from a wall scraper and/or homogenizer.

Following this, the acid form of the surfactant can be neutralized by alkali (such as TEA or KOH) can be added as required through the hopper slowly, with continued high shear from the wall scraper and/or homogenizer. Additional ingredients can then be added at this stage (including any surfactant materials which are to be added by coextrusion or injection), and the composition can then be cooled at room temperature, and perfume and preservatives are then added. The pH is checked and adjusted, and finally any suspended particles which are required are added, optionally whilst the composition is subjected to vacuum and low shear from the wall scraper only, before the composition is discharged.

Alternatively, in place of the steps above prior to the initial cooling to 20° C., a micro rotator line can be used to shear the water, polymer and optionally polyol mixture, and to subsequently cool the mixture form 90° C. to 20° C. The resulting polymer shear gel can then be processed according to the remainder of the steps above.

Polymer Types

Compositions of this invention contain a polymer or polymer mixture capable of forming a reversible gel. It is desirable that the polymer should be capable of forming a gel without requiring metal salt to be present. (Polymers which require ionic species to be present as a prerequisite for gel formation are apt to be destabilised by surfactant, even if formed as shear gel particles). Generally, this means that such a polymer, dissolved in demineralised water at some concentration between 0.1 and 10% by weight will form a gel on cooling the solution without agitation from an elevated temperature of 90° C. to 20° C. for 24 hours.

In this test of gel-formation, a polymer may or may not form a gel at every concentration in the range from 1 to 10% by weight. With some polymers it might be necessary to use more than 1%. With some polymers, concentrations as high as 10% by weight may not be achievable. Some polymers may form gels without standing for as long as 24 hours.

The polymer or polymer mixture which is capable of forming a reversible gel will usually be of natural origin—and specifically one or more polysaccharides will preferably be used. However, it is possible that the polymer, or one or more polymers in a mixture of polymers might be a chemically modified natural polymer such as a polysaccharide which has been chemically treated to provide or alter substituent groups thereon. It is also conceivable that a polymer mixture might contain a synthetic polymer together with a natural polymer. Usually however, the polymer which is used will include a polysaccharide chain of natural origin.

One polysaccharide which may be used is agar, which is of course well known for use as a growth medium for microorganisms in vitro.

Agarose is a linear polysaccharide, basically made up from β-1,3 galactose residues alternating with α-1,4 galactose residues. The latter are present as the 3,6-anhydride and are the L-enantiomer.

Agaropectin likewise has β-1,3 galactose residues alternating with α-1,4-L-galactose residues, but includes sulphate, pyruvate and/or glucuronic acid residues.

The term agar covers a family of polymers containing agarose and/or agaropectin, ie polymers with backbone structure containing alternating 1,3-D-galactose and 1,4-L-galactose residues.

Agar is extracted from certain species of red seaweed, principally in Japan. A description of agar is given by Tetsujiro Matsuhashi as Chapter 1 in "Food Gels" edited by Peter Harris, Elsevier, 1990.

Another category of polysaccharide which may be used is the kappa carrageenan. Carrageenans are a class of polysaccharides which occur in some other red seaweed species. They are linear polysaccharides made up from alternating β-1,3- and α-1,4-linked galactose residues. The 1,4-linked residues are the D-enantiomer and sometimes occur as the 3,6-anhydride. Many of the galactose residues are sulphated.

A number of carrageenan structures have been described and commercial materials are available which approximate to the ideal structures. However, variations between these structures occur, depending on the source of the carrageenan and treatment of it after extraction. A description of different carrageenan types is given in "Carrageenans" by Norman F Stanley which is Chapter 3 of "Food Gels" mentioned above.

Kappa carrageenan is sulphated on the 1,3-linked galactose residues, but not on the 1,4-linked residues. Iota carrageenan is sulphated on both residues. Lambda carrageenan has two sulphate groups on the 1,4-linked residues and one sulphate group on 70% of the 1,3-linked residues.

Other types of carrageenan may be used in mixtures with kappa. Aqueous solutions of iota carrageenan exist as reversible gels, but these appear to be self healing. Iota carrageenan can be used to form compositions in accordance with this invention, but the compositions become lumpy during storage because of the self-healing property of iota carrageenan gels, and so for this invention it is desirable to use kappa carrageenan or mixtures of kappa and iota.

Lambda carrageenan on its own in aqueous solution does not form gels because its higher charge density inhibits association between molecules and consequent structuring in liquids. However, some lambda carrageenan may be included in mixtures with kappa, or may be present as an impurity in commercial supplies of kappa or iota carrageenan.

If lambda carrageenan is included in a mixture of carrageenans, the mixture may contain a majority (more than one half of the polysaccharide) of kappa or kappa and iota carrageenan with a minority proportion of lambda carrageenan.

Another polymer which may be used is furcellaran. Furcellaran is similar to kappa carrageenan, but is only partially sulphated on the 1,3-linked galactose residues. A polymer of bacterial origin which may be used is gellan. It is the polymer of a tetrasaccharide repeat unit, containing glucose, glucuronic acid, and rhamnose residues. Tiere is some substitution with acyl groups but these are often removed during production to give a low acyl gellan. Gellans are the subject of Chapter 6 by G R Saunderson in "Food Gels" mentioned above. Another possibility is to use a so-called synergistic gel which relies on the interaction of two polymer types. In general these may be formed from a polysaccharide which is a glucomannan with sequences of mannose residues in its polymer chain, such as locust bean gum or guar gum, and a second polymer which is xanthan or carrageenan.

It is possible to include an additional thickening agent, such as a small concentration of xanthan gum, or curdlan, in the composition in addition to the gel particles. This may possibly be added after gel particles have been formed along with the surfactant.

A composition according to this invention will generally contain from 0.1 to 10 wt % of naturally occurring polymer. Normally, at least half the weight of this polymer will be one or more polymers capable of forming a reversible gel on cooling from an elevated temperature to 20° C. as a quiescent solution is demineralised water.

Polymer capable of forming a reversible gel may constitute from 0.5 to 10 wt % of the whole composition, often from 0.2 or 0.5wt % up to 5 or 8 wt %.

In general, the viscosity of a shear gel composition in accordance with this invention will increase with the concentration of polymer contained in it.

Viscosity will also be affected by the size and shape of the gel particles, which in turn is affected by the conditions used to apply shear during cooling. In general, combinations of variable cooling rates and different rotor speeds during shearing permits the optimisation of particle dispersion smoothness, suspending properties and viscosity, possibly because gel particle shapes can vary between spherical and filamentous forms.

Non-surfactant Electrolyte

Although it is generally desirable that the polymer should be capable of forming a gel without participation of ionic species, some polymers which are capable of forming a gel in distilled or demineralised water nevertheless form gels of greater viscosity if some electrolyte is present. Notably the viscosity of kappa carrageenan gel dispersions is increased by the presence of potassium ions and the viscosity of agar gel dispersions is increased in the presence of calcium ions. Consequently, a polymer solution which is cooled under shear to form gel particles as required for this invention may include electrolyte to enhance the strength of the resulting gel particles. The amount of electrolyte required may be a small percentage of the product, e.g. 1%.

Foaming Surfactant

Compositions of this invention contain at least 3 wt % of a foaming surfactant system, preferably from 5 wt % up to 30 wt %. At least half, better at least two-thirds of the surfactant present is preferably selected from anionic, amphoteric or zwitterionic surfactants, or alkylpolyglycosides or alkyl polyhydroxyamides (eg. alkyl glucamides)

which are foaming nonionic surfactants. Preferably the composition contains at least 5% anionic surfactant possibly accompanied by amphoteric or zwitterionic surfactant. Conveniently the composition comprises 5 to 25% by weight anionic surfactant, preferably 5–15% anionic surfactant.

Ethoxylated alcohols, which are low-foaming nonionic surfactants, may be present as less than half of the surfactant present. Preferably, the amount (if any) of such surfactant is not more than a quarter of the surfactant present.

One type of anionic surfactant which is frequently used in personal washing compositions, and which may be used in compositions of this invention is alkyl ether sulphate of the formula:

where $R^4$ is alkyl or alkenyl of 8 to 18 carbon atoms, especially 11 to 15 carbon atoms, t has an average value of at least 2.0 and M is a solubilising cation such as sodium, potassium, ammonium or substituted ammonium. Preferably t has an average value of 3 or more.

Other anionic surfactants may be used. Possibilities include alkyl glyceryl ether sulphates, sulphosuccinates, taurates, sarcosinates, acyl isethionates, sulphoacetates, alkyl phosphates, acyl amino carboxylates, acyl lactates and soap. In certain embodiments acyl amino carboxylate surfactants are particularly preferred.

Sulphosuccinates may be monoalkyl sulphosuccinates having the formula:

and amido-MEA sulphosuccinates of the formula:

wherein $R^5$ ranges from $C_8$–$C_{20}$ alkyl, preferably $C_{12}$–$C_{15}$ alkyl and M is a solubilising cation (such as those above).

Sarcosinates generally have by the formula $R^5CON(CH_3)CH_2CO_2M$, wherein $R^5$ ranges from $C_8$–$C_{20}$ alkyl, preferably $C_{12}$–$C_{15}$ alkyl and M is a solubilising cation (such as those above). Taurates are generally identified by the formula $R^5CONR^6CH_2CH_2SO_3M$, wherein $R^5$ ranges from $C_8$–$C_{20}$ alkyl, preferably $C_{12}$–$C_{15}$ alkyl, $R^6$ ranges from $C_1$–$C_4$ alkyl and M is a solubilising cation (such as those above).

Fatty acyl isethionates have the formula:

where R is an alkyl group of 7 to 21 carbon atoms and M is a solubilising cation such as those above.

Another class of foaming anionic surfactants are the long chain alkyl carboxylates and alkyl ether carboxylates of general formula:

Where M is a monovalent akali cation such as Na and/or K, or an organic cation such as ammonium, monoethanolammonium or triethanolammonium, a is an integer from 0 to about 7, and R is a straight or branched chain, saturated or unsaturated hydrocarbon group having from about 10 to about 20 carbon atoms.

A further class of suitable anionic surfactants are monoalkyl phosphate and dialkyl phosphate surfactants, such as for example dioctyl phosphate, as well as ether carboxylate and ethoxylated citrate surfactants.

The anionic detergent included in the composition will generally be selected to avoid harsh detergent such as primary alkane sulphonate or alkyl benzene sulphonate. The amount, if any, of these is preferably less than 3% of the detergents present.

Anionic surfactant may be used jointly with amphoteric/zwitterionic surfactant, notably betaine or sulphobetaine.

Amphoteric/zwitterionic surfactants for use in this invention will usually comply with an overall structural formula where $R^1$ is alkyl or alkenyl of 7 to 18 carbon atoms $R^2$ and $R^3$ are each independently alkyl, hydroxyalkyl or carboxyalkyl of 1 to 3 carbon atoms m is 2 to 4 n is 0 or 1

X is alkylene of 1 to 3 carbon atoms optionally substituted with hydroxyl, and Y is $-CO_2^-$ or $-SO_3^-$ Suitable amphoteric/zwitterionic detergents within the above general formula include simple betaines of formula:

and amido betaines of formula:

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the zwitterionic detergent is a sulphobetaine of one of the formulae:

where m is 2 or 3, or variants of these in which $-(CH_2)_3SO_3^-$ is replaced by Another class of amphoteric surfactants are the alkylamide alkyl amines, especialy the amphoacetates of general formula:

where M is Na, K, ammonium or triethanolammonium, an R is branched or straight chain saturated or unsaturated alkyl group having about 10 to about 20 atoms. Glycoside surfactants are nonionic in character and of course includes glycoside residues. Suitably they are of the general formula:

$$RO(R'O)_t(G)_x \text{ or } RCO_2\text{—}(R'O)_t(G)_x.$$

in which G is a residue of a pentose or hexose, R'O is an alkoxy group, x is at least unity and R is an organic hydrophobic group from 6 to 20 carbon atoms which is preferably aliphatic, either saturated or unsaturated, notably straight or branched alkyl, alkenyl, hydroxyalkyl or hydroxyalkenyl. Particularly, R may be alkyl or alkenyl of 7 to 14 or 16 carbon atoms.

The value of t in the general formulae above is preferably zero, so that the —(R'O)$_t$— unit of the general formulae is absent. In that case the general formulae become:

If t is non-zero, it is preferred that R'O is an ethylene oxide residue. Other possibilities are propylene oxide and glycerol residues. If the parameter t is non-zero so that R'O is present, the value of t (which may be an average value) will preferably lie in the range from 0.5 to 10.

The group G is typically derived from fructose, glucose, mannose, galactose, talose, gulose, allose, altrose, idose, arabinose, xylose, lyxose and/or ribose. Preferably, the G is provided substantially exclusively by glucose units. Intersaccharide bonds may be from a 1-position to a 2, 3, 4 or 6-position of the adjoining saccharide. Hydroxyl groups on sugar residues may be substituted., e.g. etherified with short alkyl chains of 1 to 4 carbon atoms. Preferably a sugar residue bears no more than one such substituent.

The value x, which is an average, is usually termed the degree of polymerization. Desirably x varies between 1 and 8. Values of x may lie between 1 and 3, especially 1 and 1.8.

Alkyl polyglycosides of formula RO(G)$_x$, i.e. a formula as given above in which t is zero, are available from Horizon Chemical Company, BASF and Henkel.

O-alkanoyl glucosides of formula RCO$_2$—(G)$_x$ are described in International Patent Application WO 88/10147 (Novo Industri A/S). In particular the surfactants described therein are glucose esters with the acyl group attached in the 3- or 6-position such as 3-O-acyl-D-glucose or 6-O-acyl-D-glucose. Notable are 6-0-alkanoyl glucosides, in which the alkanoyl group incorporates an alkyl or alkenyl group having from 7 to 13 carbon atoms. The glucose residue may be alkylated in its 1-position with an alkyl group having from 1 to 4 carbon atoms, such as ethyl or isopropyl. Alkylation in the 1-position enables such compounds to be prepared by regiospecific enzymatic synthesis as described by Bjorkling et al. (J. Chem. Soc., Chem. Commun. 1989 p934).

Aldobionamides are amides of an aldobionic acid or aldobionolactone. Aldobionic acids are disaccharides or polysaccharides in which the aldehyde group (generally found at the C$_1$ position of the sugar) has been replaced by a carboxylic acid. Upon drying they cyclise to aldobionolactones. The disaccharide may in particular be lactose or maltose, so that the aldobionamide is a lactobionamide or maltobionamide. Further information about aldobionamides and their preparation is given in EP-A-550278.

Descriptions of alkyl polyhydroxy fatty acid amides are found in U.S. Pat. No. 2,965,576, EP 220676, EP 550557 and documents referred to therein. Polyethylene oxide-polyproylene oxide copolymers are marketed commercially, e.g. under the trademark Pluronic.

The foaming properties of surfactants may be evaluated by a test carried out using a panel of assessors. A suitable number of assessors to provide the panel is 20. Each panellist wears surgical gloves, turned inside out, which are first washed with soap to remove any powder, eg talc, from their surface, and dried. Test solutions are prepared containing 2% by weight of surfactant in demineralised water. To carry out each test, 2.5 ml of a test solution is dosed slowly from a syringe directly on to the dry gloves. The panellist then rubs his or her hands together both during and after dosing the surfactant solution onto them, so as to generate a lather. The panellist takes care to avoid dropping solution from the hands. The panellist continues to generate lather by rubbing their hands together for about 10 to 20 seconds until the volume of lather is perceived as constant after which the volume of lather on the gloves is measured by the panellist submersing their hands into a bowl of water while a calibrated collecting funnel is held above them so that the lather is swept off the hands into the collecting funnel. The results obtained from each panellist are averaged.

A surfactant can be designated as a foaming surfactant if the volume of foam obtained is greater than 10 cm$^3$. An alternative definition is to state that the volume of foam for a foaming surfactant should be at least half the volume generated from the same volume of an equivalent concentration solution of sodium lauryl ethyl sulphate containing average 3 ethylene oxide residues.

A number of surfactants were tested in accordance with the above procedure and the following results were obtained.

| Surfactant (2 wt % total surfactant) | | Geometric mean of |
| --- | --- | --- |
| Trade name | Abbreviation | foam volumes/cm$^3$ |
| Brij 58 | C$_{16}$E$_{20}$ | 3.390 |
| Genapol ZRO | SLES | 21.500 |
| Dehyton K | CAPB | 35.726 |
| Genapol ZRO with Dehyton K | SLES/CAPB (13:2 weight ratio) | 19.303 |
| Plantaren 2000 UP | APG | 47.705 |
| Genapol ZRO with Dehyton K and Brij 58 | SLES/CAPB/C$_{16}$E$_{20}$ (13:2:5 weight ratio) | 14.815 |
| Jordapon CI with Dehyton K | SCI/CAPB (13:2 weight ratio) | 27.667 |

Brij 58, supplied by ICI, is C16 fatty alcohol ethoxylated with average 20 ethylene oxide residues (C$_{16}$E$_{20}$).

Genopol ZRO, supplied by Hoechst, is sodium lauryl ether sulphate containing average 3 ethylene oxide residues (SLES).

Dehyton K, supplied by Henkel, is coconut amidopropyl betaine (CAPB)

Plantaren 2000 UP, supplied by Henkel, is an alkyl poly glucoside in which the alkyl chain has average 10 carbon atoms and the molecules contain an average of 1.4 glucoside residues. Jordapon CI, supplied by PPG Mazer, is sodium cocoyl isethionate (SCI).

In a preferred embodiment the composition contains relatively high levels of polyol materials. Typically, polyol compounds may be present at levels of up to 90% by weight, more typically 2–60% by weight, more preferably 5–50% by weight, even more preferably 10–45% by weight of the composition.

Suitable polyol materials include glycerol, sorbitol, hexanetriol, propan-1,2 diol, 1,3 butylene glycol, hexylene glycol and propylene gylcol, as well as polyethylene glycols and polypropylene gylcols. Suitable polyethylene and polypropylene glycols typically have a molecular weight in the region 100–4000, more preferably 200–2000. A preferred polyol material is glycerol.

The inclusion of a polyol material in compositions according to the invention has been found to provide a variety of benefits. In the first instance, compositions according to the invention which contain relatively high levels of polyols have been found to have improved stability when subjected to freeze/thaw stability test cycling. In addition, compositions containing high levels of polyols have been found to have relatively good integrity, in particular in terms of their viscosity and their ability to suspend particles.

Compositions containing polyols may also have improved clarity, in particular as the need to provide more direct structuring of the product (for example by using clays or carbomer polymers) is reduced. The inclusion of high levels of polyols may also facilitate the includions and gelling of benefit agents in the composition. Also, the inclusion of high levels of polyol, together with the use of the polymer or polymer mixture may provide surprising improvements in foam stability creaminess of lather.

Further, the use of relatively high levels of polyols has been found to reduce the reliance of the system on co-structurants (such as clays) with the polymer or polymer mixture. Hence, it has been found that such compositions may have a reduced need for water in the system, since less water is required for hydration of the co-structurant, which in practice increases the options to the skilled practitioner in terms of the surfactant systems which may be used or accommodated in the composition.

The use of high levels of polyols in systems has also been found to be advantageous from a processing perspective, since as is mentioned elsewhere in the application, it is desirable that surfactants are added to the polymer mixture after it has been formed and cooled, to avoid phase separation. The addition of relatively high levels of polyols can result in the shifting of the phase boundary for the composition, meaning that low viscosity isotropic liquids may form. These are relatively easy to process compared to the high viscosity liquid crystal phases (such as H1 or cubic) which can otherwise form in certain circumstances.

Other materials may be included in compositions of this invention. Possibilities include colouring agents, opacifying agents, organic polymers, perfumes including deodorant perfumes, bactericidal agents to reduce the microflora on skin, antioxidants and other preservatives.

Compositions according to the invention can optionally contain a benefit agent. The benefit agent can be an emollient oil by which is meant a substance which softens the skin (stratum corneum) directly or by increasing water content and keeping it soft by retarding decrease of water content.

Suitable emollients and benefit agents include:
(a) silicone oils, gums and modifications thereof such as linear and cyclic polydimethylsiloxanes; amino, alkyl alkylaryl and aryl silicone oils;
(b) fats and oils including natural fats and oils such as jojoba, soybean, rice bran, avocado, almond, olive, sesame, persic, castor, coconut, mink oils; cacao fat; beef tallow, lard; hardened oils obtained by hydrogenating the aforementioned oils, and synthetic mono, di and triglycerides such as myristic acid glyceride and 2-ethylhexanoic acid glyceride;
(c) waxes such as carnauba, spermaceti, beeswax, lanolin and derivatives thereof;
(d) hydrophobic plant extracts;
(e) hydrocarbons such as liquid paraffins, vaseline, petrolatum, microcrystalline wax, ceresin, squalene, pristan and mineral oil;
(f) higher fatty acids such as lauric, myristic, palmitic, stearic, behenic, oleic, linoleic, linolenic, lanolic, isostearic and poly unsaturated fatty acids (PUFA);
(g) higher alcohols such as lauryl, cetyl, stearyl, oleyl, behenyl, cholesterol and 2-hexydecanol alcohol;
(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;
(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;
(j) lipids such as cholesterol, ceramides, sucrose esters and pseudo-ceramides as described in European Patent Specification No. 556,957;
(k) vitamins such as vitamin A and E, and vitamin alkyl esters, including those vitamin C alkyl esters;
(l) sunscreens such as octyl methoxyl cinnamate (Parsol MCX) and butyl methoxy benzoylmethane (Parsol 1789);
(m) phospholipids;
(n) antimicrobial agents;
(o) hydroxy acids such as alpha and beta hydroxy acids;
(p) catonic polymers to condition skin or aid skin benefit agent deposition; and
(q) mixtures of any of the foregoing components.

A particularly preferred benefit agent is silicone, preferably silicones having viscosity greater than about 50,000 centipoise. One example is polydimethylsiloxane having viscosity of about 60,000 centistokes.

The benefit agent may typically be present in compositions according to the invention at levels of 0.1–20% by weight.

EXAMPLE 1

A number of compositions were prepared containing carrageenan together with surfactant. The carrageenans which were used are set out in the following table.

| Material Name | Trade Name | Supplier |
| --- | --- | --- |
| Kappa carrageenan | Genugel X0909 | Hercules |
| Iota carrageenan | Genuviso X0908 | Hercules |
| Lambda carrageenan | Genugel X-3948 | Hercules |

Two surfactants were used:
Sodium lauryl ether sulphate, average 3EO, (SLES) and coconut amidopropyl betaine (CAPB) supplied by Goldschmidt as Tegobetaine CK.

The surfactants were used in a constant ratio of 13 parts SLES to 2 parts CAPB. The general method of preparation was to dissolve the surfactants in demineralised water to make up a concentrated solution (25% wt surfactant) at 60–70° C. The polymer in powdered form was dissolved in demineralised water at 90–100° C. Appropriate quantities of the two solutions were then mixed to form a solution containing 10% wt surfactant and a chosen concentration of polymer. Electrolyte was added to this solution. The mixed solution was placed in the vessel of a TK Agi Homo mixer as described earlier with reference to FIG. 1. This mixer was run at 100 rpm, while the composition was cooled in the mixer from 75° C. to 20° C. over a period of 60 minutes.

The compositions prepared are set out in the following table:

| No | Kappa (wt %) | Iota (wt %) | Lambda (wt %) | KCl (wt %) | CaCl$_2$ (wt %) | Propan-1,2-diol (wt %) |
|---|---|---|---|---|---|---|
| 1 | 1.5 | — | — | 0.26 | — | — |
| 2 | 2 | — | — | 0.26 | — | — |
| 3 | 2.5 | — | — | 0.26 | — | — |
| 4 | 3 | — | — | 0.26 | — | — |
| 5 | 4.6 | — | — | 0.26 | — | 5 |
| 6 | 2 | — | — | 0.50 | — | — |
| 7 | 1 | 1 | — | 0.26 | 0.62 | — |
| 8 | 2 | 0.3 | — | 0.26 | — | — |
| 9 | 2 | — | 0.3 | 0.26 | — | — |
| 10 | 2 | — | 0.6 | 0.26 | — | — |
| 11 | 2 | — | 1 | 0.26 | — | — |

Comparison of samples 1 to 5 show a small but progressive increase in viscosity with kappa concentration up to 3% kappa. At 4.6% kappa, the system is stiff and paste-like, but still spreads easily on rubbing (the propan-1, 2-diol was added to the surfactant stock solution to allow greater concentrations to be used without forming hexagonal phase). Increasing the concentration of KCl to 0.5% (sample 6), to increase gel strength, does not appear to result in a more viscous system.

Samples 7 and 8, containing some iota carrageenan, had similar properties to sample 2 but were somewhat more elastic as a consequence of their iota carrageenan content.

The effect of lambda (samples 9, 10 and 11) is to enhance smoothness but without greatly influencing viscosity.

A quantity of the shear gel of sample 4 containing 3 wt % kappa carrageenan was reheated to 70° C. and then allowed to cool to room temperature without agitation. The result was a rigid gel, indicating that the mobility of the composition formed under shear must be attributed to transformations of the carrageenan solution into small particles of gel during cooling.

EXAMPLE 2

Samples 4, 8 and 10 from the previous example were packed in 150 ml translucent polyethylene tubes with 1.5 mm diameter outlets.

These samples were assessed by 24 female panellists who were instructed to observe the visual appearance and flow of the products in the tube, then squeeze some of the composition from the tube onto a transparent plastic sheet and make a visual observation of the product, then feel the product with their finger tips. Subsequently they were asked to wash their forearms using each of the products. As a comparison the panellists were provided with a conventional shower gel in which surfactant was thickened by incorporation of salt.

The panellists generally commented that the products of this invention were less sticky or stringy than the control composition and that when dispensed from the tube the dispensed material was less prone to slump under its own weight. (That observation can be attributed to the strongly shear-thinning character of the products of the invention.) When used for washing, the products of the invention were perceived as clean rinsing i.e. they were observed to leave little or no residue or tackiness on the skin after drying.

EXAMPLE 3

Agar shear gels were prepared. The agar was "Deltagar LTS" from Quest International's facility at Kilnagleary, Carriglane, Co. Cork, Ireland. Xanthan, supplied as "Keltrol F" by Kelco was also used. The agar or mixture of agar and xanthan was dissolved in demineralised water and cooled from 75° C. to 20° C. The concentrations of polymers, and the viscosities of the resulting compositions were:

| Agar (wt %) | Xanthan (wt %) | Viscosity at $10^{-1}$ sec (mPa · s) | Approx bead diameter ($\mu$m) |
|---|---|---|---|
| 1 | — | 1800 | 100–200 |
| 2 | — | 3000 | 50–150 |
| 2 | 0.05 | 5000 | 50–100 |
| 4 | — | 18000 | 10–30 |

The compositions were examined under a microscope. Gel beads, of approximate size indicated in the table, were observed. At 1% and 2% agar, the beads could be seen to have small filaments projecting from them.

Inclusion of the small concentration of xanthan led to the formation of slightly smaller beads with fewer filaments projecting from them. The composition was notably smoother and less viscous.

Compositions containing 2% and 4% agar were mixed with concentrated aqueous solutions of surfactant (25 wt %) in proportion to give a composition containing 10 wt % surfactant (13:2 SLES:CAPB as in Example 1). Mixing was carried out in a beaker,at 20° C. using a paddle stirrer turned by an overhead motor at sufficiently low speed to avoid incorporating bubbles.

EXAMPLE 4

Shower Gel

A shower gel was made in the following way using apparatus generally shown in FIG. 2, but without heat exchanger A3. Agar, calcium chloride, potassium sorbate and sorbic acid were dissolved in hot water (>90° C.) using a Silverson stirrer. The resulting hot agar solution (M) was transferred to tank T1 which was a 5 litre jacketed tank fitted with a bottom stirrer, baffle and hermetically sealing lid and maintained at 95° C. It was stored in this tank for 30 min. A surfactant mixture was made by diluting two parts of a 70% active sodium lauryl ether sulphate (SLES)(Manro BES) paste with one part of propylene glycol to form a 46.7% active surfactant solution. To this solution was added 100% active cocoamido propyl betaine (Tegobetaine CK) (CAPB) in an amount to achieve a ratio of 13 parts SLES to 2 parts CAPB. Colourants, perfume and antioxidant were added as desired and the final surfactant solution (N) transferred to tank T2 which was a second jacketed, stirred 5 litre tank maintained at 30° C. Aeration of the mix was avoided by limiting the stirrer speed to <60 r.p.m. The compositions of the solutions (M) and (N) are set out in the following table together with the compositions containing a total of 16% surfactant.

COMPOSITIONS - EXAMPLE 4

| Material | Solution M (% w/w) | Solution N (% w/w) | Product Composition (% w/w) |
|---|---|---|---|
| Agar (Luxara 1253) | 4.50 | — | 3.00 |
| Potassium sorbate | 0.10 | — | 0.07 |
| Sorbic acid | 0.40 | — | 0.28 |
| Calcium Chloride 2H$_2$O | 3.38 | — | 2.30 |
| SLES (pure) | — | 43.28 | 13.867 |
| CAPB (100% active) | — | 6.68 | 2.133 |
| Pigments | — | 0.00447 | 0.003 |
| Propylene glycol | — | 13.65 | 9.29 |
| De-ionised water | 91.62 | 36.39 | 69.06 |

A microvotator line with layout as illustrated by FIG. 2 contained the jacketed tank T1, connected to one channel P1 of a proportioning piston pump and thereafter to two scraped surface heat exchangers A1 and A2, each of about 15 ml volume arranged in series. The jacketed feed tank T2, was connected to a second channel P2 of the proportioning pump and thence to one end of a pinned crystallising mixer C of about 150 ml volume. Jacket temperatures of these units were controlled by glycol, heated or cooled by appropriately sized circulating baths.

Hot water (95° C.) was pumped through the votator line to pre-warm the units and feed lines. Agar solution (M) was then pumped through the line with the pump P1 set at 100% until a shear gel was formed. This material was either fed to waste or re-worked to the feed tank T1, Meanwhile, surfactant solution (N) was pumped (P2 set at 47%) through the mixer C with its rotor stationary. When full, the rotor of the mixer C was started and set to 500 r.p.m. The shear gel formed from solution (M) was fed to a port located centrally in the barrel of the mixer C. The shower gel thus formed has a composition as set out in the table above under the heading "Product Composition". It was collected from the outlet of the mixer C and packaged in plastic bottles. Typical run conditions are set out in the following table:

PROCESS CONDITIONS - EXAMPLE 4

|  | T1 | T2 | P1 | P2 | A1 | A2 | C |
|---|---|---|---|---|---|---|---|
| Jacket Temperature ° C. | 95 | 30 | — | — | 75 | 0 | 30 |
| Product Exit Temperature ° C. | — | — | 56.7 | — | 69.1 | 12.9 | 26 |
| Rotor Speed r.p.m | <60 | <60 | — | — | 1000 | 2000 | 500 |
| % Pump Stroke | — | — | 100 | 47 | — | — | — |

A phase stable, viscous, foaming and essentially transparent shower gel was produced exhibiting a peaking ability (ie shape sustaining character), upon being squeezed from the bottle. The product had an excellent non-stringy thinning behaviour in use and left the skin feeling smooth but not sticky when dry.

EXAMPLE 5
Moisturising Shower Gel Base

A moisturising shower gel was made in a similar way to Example 4. Agar, sodium caseinate, potassium sorbate and sorbic acid were dissolved in hot water (>90° C.) using a Silverson stirrer. The hot solution was maintained at 90° C. in tank T1 for 30 min. prior to use. An oil phase was dispersed in the agar solution using a homogeniser (Crepaco) to achieve average oil droplet sizes of around 1 micron in the resulting emulsion M. A foaming surfactant composition N (approximately 50% active) was placed in a separate tank and maintained at 30° C. with slow stirring (<60 r.p.m.). The compositions of the solutions M and N are set out in the following table, together with the composition of the product made from them, which contained a total of 10% surfactant.

The oil droplets remained in suspension in the product composition.

COMPOSITIONS - EXAMPLE 5

| Material | Solution M (% w/w) | Solution N (% w/w) | Product Composition (% w/w) |
|---|---|---|---|
| Agar (Luxara 1253) | 4.00 | — | 3.17 |
| Potassium sorbate | 0.10 | — | 0.08 |
| Sorbic acid | 0.40 | — | 0.32 |
| Sodium Caseinate (DMV) | 2.00 | — | 1.60 |
| SLES (pure) | — | 43.28 | 8.667 |
| CAPB (100% active) | — | 6.66 | 1.333 |
| Oil Blend | 10.00 | — | 7.94 |
| Propylene glycol | — | 13.65 | 9.29 |
| De-ionised water | 83.50 | 36.41 | 67.60 |

The solutions M and N were processed using the microvotator line and procedure of Example 4. The run conditions were as set out in the table below. The product was a thick, white, foaming shower gel exhibiting good thinning but non-stringy flow properties in use. It left skin feeling smooth and moist.

PROCESS CONDITIONS - EXAMPLE 5

|  | T1 | T2 | P1 | P2 | A1 | A2 | C |
|---|---|---|---|---|---|---|---|
| Jacket Temperature ° C. | 95 | 30 | — | — | 95 | 5 | 5 |
| Product Exit Temperature ° C. | — | — | 68.0 | — | — | 22.9 | 8.6 |
| Rotor Speed r.p.m | <60 | <60 | — | — | 1000 | 2000 | 1000 |
| % Pump Stroke | — | — | 100 | 26 | — | — | — |

EXAMPLE 6
Moisturising Shower Gel Base

Example 5 was repeated but omitting the emulsifier (sodium caseinate). The product was a stable, thick, white gel. It was essentially non-foaming when initially applied to the skin, behaving more like a cleansing cream but formed copious amounts of foam upon dilution with water during normal washing action, leaving skin feeling smooth and moist. The compositions of solutions M and N and the product are set out in the following table:

COMPOSITIONS - EXAMPLE 6

| Material | Solution M (% w/w) | Solution N (% w/w) | Product Composition (% w/w) |
|---|---|---|---|
| Agar (Luxara 1253) | 4.00 | — | 3.17 |
| Potassium sorbate | 0.10 | — | 0.08 |

-continued

COMPOSITIONS - EXAMPLE 6

| Material | Solution M (% w/w) | Solution N (% w/w) | Product Composition (% w/w) |
|---|---|---|---|
| Sorbic acid | 0.40 | — | 0.32 |
| SLES (pure) | — | 43.28 | 8.667 |
| CAPB (100% active) | — | 6.66 | 1.333 |
| Oil Blend | 10.00 | — | 7.94 |
| Propylene glycol | — | 13.65 | 9.29 |
| De-ionised water | 81.50 | 36.41 | 66.03 |

EXAMPLE 7

Thick Moisturising Shower Gel Base Example 5 was repeated using a higher agar concentration, with sodium caseinate replaced by gelatin (Bloom 150) and with the addition of calcium chloride to solution M. The surfactant solution N was unchanged. The compositions are set out in the following table:

COMPOSITIONS - EXAMPLE 7

| Material | Solution M (% w/w) | Solution N (% w/w) | Product Composition (% w/w) |
|---|---|---|---|
| Agar (Luxara 1253) | 4.50 | — | 3.20 |
| Potassium sorbate | 0.10 | — | 0.08 |
| Sorbic acid | 0.40 | — | 0.32 |
| Gelatin (Bloom 150, Extraco) | 0.75 | — | 0.60 |
| Calcium Chloride 2H$_2$O | 2.876 | — | 2.30 |
| SLES (pure) | — | 43.28 | 8.667 |
| CAPB (100% active) | — | 6.66 | 1.333 |
| Oil Blend | 12.502 | — | 10.000 |
| Propylene glycol | — | 13.65 | 9.29 |
| De-ionised water | 81.00 | 36.41 | 63.65 |

The votator line process conditions were as set out in the following table:

PROCESS CONDITIONS - EXAMPLE 7

| | T1 | T2 | P1 | P2 | A1 | A2 | C |
|---|---|---|---|---|---|---|---|
| Jacket Temperature ° C. | 95 | 30 | — | — | 95 | 5 | 5 |
| Product Exit Temperature ° C. | — | — | 64.1 | — | 69.1 | 8.7 | 8.3 |
| Rotor Speed r.p.m | <60 | <60 | — | — | 1000 | 2000 | 1000 |
| % Pump Stroke | — | — | 100 | 26 | — | — | — |

EXAMPLE 8

Hair Shampoo Base

A preparation of very high viscosity and high surfactant active concentration was made containing a typical foaming, hair cleansing surfactant phase so as to permit dilution during further processing into a hair shampoo. As in Example 4, agar was dissolved together with potassium sorbate, sorbic acid and calcium chloride in hot water (>90° C.) using a Silverson mixer to form agar solution M.

A surfactant mixture was made by diluting two parts of a 70% active sodium lauryl ether sulphate (SLES)(Manro BES) paste with one part of propylene glycol to form a 46.7% active surfactant solution. To this solution was added 100% active cocoamido propyl betaine (Tegobetaine CK) (CAPB) in an amount to achieve a ratio of 13 parts SLES to 2 parts CAPB. Antioxidant was added and the final solution (N) transferred to a feed tank maintained at 30° C. Aeration of the mix was avoided by limiting the stirrer speed to <60 r.p.m. The compositions of solutions M and N and of the high-viscosity composition made from them which contained 24% surfactant, are set out in the following table:

COMPOSITIONS - EXAMPLE 8

| Material | Solution M (% w/w) | Solution N (% w/w) | Product Composition (% w/w) |
|---|---|---|---|
| Agar (Luxara 1253) | 4.5 | — | 2.25 |
| Potassium sorbate | 0.10 | — | 0.05 |
| Sorbic acid | 0.40 | — | 0.21 |
| Calcium Chloride 2H$_2$O | 3.38 | — | 1.76 |
| SLES (pure) | — | 43.28 | 21.00 |
| CAPB (100% active) | — | 6.24 | 3.00 |
| Pigments | — | 0.00 | 0.00 |
| Propylene glycol | — | 13.65 | 15.00 |
| De-ionised water | 91.62 | 36.83 | 56.73 |

The processing of the two solutions was carried out using the micro-votator line design and method of Example 4. The process run conditions are set out in the following table:

PROCESS CONDITIONS - EXAMPLE 8

| | T1 | T2 | P1 | P2 | A1 | A2 | C |
|---|---|---|---|---|---|---|---|
| Jacket Temperature ° C. | 95 | 30 | — | — | 75 | 5 | 5 |
| Product Exit Temperature ° C. | — | — | 64.1 | — | 69.1 | 8.7 | 8.3 |
| Rotor Speed r.p.m | <60 | <60 | — | — | 500 | 2500 | 1000 |
| % Pump Stroke | — | — | 100 | 92 | — | — | — |

EXAMPLE 9

Carrageenan Bsed Surfactant Gel

A stable, foaming surfactant gel was made using mixed xanthan and carrageenans. Xanthan (Keltrol F, Kelco International Ltd), pure iota-carrageenan (Genuvisco X-0908, Hercules) and pure kappa-carrageenan (Genugel X-0909, Hercules) powders were dry blended and then dissolved in hot deionised water (>80° C.) using a Silverson stirrer to which potassium sorbate and sorbic acid were added. The hot solution (M) was transferred to a stirred, jacketed feed tank and maintained at 85° C. A surfactant mixture was made by diluting two parts of a 70% active sodium lauryl ether sulphate (SLES)(Manro BES) paste with one part of propylene glycol to form a 46.7% active surfactant solution. This solution was heated to 60° C. and the 100% active cocoamido propyl betaine (Tegobetaine CK) (CAPB) added in an amount to achieve a ratio of 13 parts SLES to 2 parts CAPB This solution (N) was added to the hot polymer solution M in the feed tank and processed through a micro-votator line comprising feed tank, proportioning pump and a succession of three scraped surface heat exchangers designated A1, A2, A3. The compositions and the process conditions are set out in the following two tables:

COMPOSITIONS - EXAMPLE 9

| Material | Solution M (% w/w) | Solution N (% w/w) | Product Composition (% w/w) |
|---|---|---|---|
| Kappa carrageenan | 1.0 | — | 0.80 |
| Iota carrageenan | 1.5 | — | 1.20 |
| Xanthan | 0.10 | — | 0.08 |
| Potassium sorbate | 0.20 | — | 0.05 |
| Sorbic acid | 0.40 | — | 0.21 |
| SLES (pure) | — | 43.28 | 8.67 |
| CAPB (100% active) | — | 6.68 | 1.33 |
| Propylene glycol | — | 7.74 | 6.19 |
| De-ionised water | 96.80 | 42.30 | 81.47 |

PROCESSING CONDITIONS - EXAMPLE 9

| | T1 | P2 | A1 | A2 | A3 |
|---|---|---|---|---|---|
| Jacket Temperature (° C.) | 85 | — | −5 | 0 | 0 |
| Product Exit Temperature (° C.) | — | 43.1 | 9.4 | 0.7 | 2.8 |
| Rotor Speed r.p.m | <60 | — | 2500 | 1000 | 1000 |
| % Pump Stroke | — | 100 | — | — | — |

EXAMPLE 10

Liquid Soap

The composition of the previous Example was processed in a different way to produce a liquid soap product. Carrageenans, sorbic acid and potassium sorbate were dissolved in hot water (<80° C.) with stirring as before to form solution M which was maintained at this temperature in a stirred tank. Xanthan was dispersed in de-ionised water, heated to 95° C. and maintained at this temperature in a second stirred tank T2 (solution X). Surfactant solution (N) was prepared as in Example 6 and held in a third stirred tank T3 at 30° C.

Figure 3:
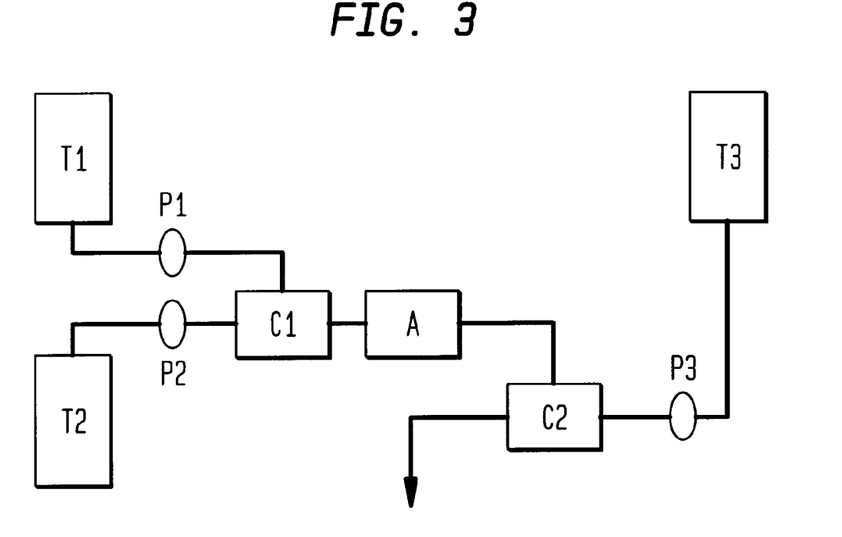

A micro-votator process line as illustrated by FIG. 3 was used. It was constructed such that solution X was fed from tank T2 through one end of a mixer C1 while carrageenan solution M was fed from tank T1 to a centrally located port on the same mixer. Cooling and shear-gel formulation took place in this mixer. After passing through a scraped surface heat exchanger A to complete cooling, the mixture was delivered to the centrally located port of a second mixer C2 through which solution N from tank T3 was already flowing.

Processing conditions are set out in the following table:

PROCESS CONDITIONS - EXAMPLE 10

| | T1 | T2 | T3 | P1 | P2 | P3 | C1 | A1 | C2 |
|---|---|---|---|---|---|---|---|---|---|
| Jacket Temperature ° C. | 95 | 95 | 30 | — | — | — | 75 | 5 | 5 |
| Product Exit Temperature ° C. | — | — | — | 57 | — | — | 14.4 | 7.4 | 10.6 |
| Rotor Speed r.p.m. | <60 | <60 | <60 | — | — | — | 2000 | 1000 | 1000 |
| % Pump Stroke | — | — | — | 85 | 15 | 43 | — | — | — |

EXAMPLE 11

Fabric Wash Liquid Base

A foaming surfactant preparation intended for use in machine washing of fabrics was made using a micro-votator line of the type shown in FIG. 2 and described in Example 4. Agar, calcium chloride, potassium sorbate and sorbic acid were dissolved in hot water (>90° C.) using a Silverson stirrer. The hot solution (M) was transferred to a jacketed tank T1 fitted with a bottom stirrer, baffle and hermetically sealing lid and maintained at 95° C. for 30 min. A surfactant mixture was made by diluting a 70% active sodium lauryl ether sulphate (SLES)(Manro BES) paste with propylene glycol and a mixture of non-ionic and anionic surfactants. Colourants, perfume and preservative were added as desired and the resulting solution (N) with composition shown in the table below was transferred to a feed tank T2 maintained at 30° C. Aeration of the mix was avoided by limiting the stirrer speed to below 60 r.p.m. The processing was as in Example 4. The product composition was in the form of an optically clear liquid capable of suspending particles of insoluble solids. It contained a total of 22.9% surfactant.

The compositions and the process conditions are set out in the following two tables:

COMPOSITIONS - EXAMPLE 11

| Material | Solution M (% w/w) | Solution N (% w/w) | Product Composition (% w/w) |
|---|---|---|---|
| Agar (Luxara 1253) | 3.00 | — | 1.24 |
| SLES (pure) | 0.0 | 18.54 | 10.86 |
| Non-foaming Surfactant mixture | 0.0 | 20.55 | 12.04 |
| Propylene glycol | — | 10.17 | 5.96 |
| De-ionised water | 97.00 | 50.74 | 69.90 |

PROCESS CONDITIONS - EXAMPLE 11

| | T1 | T2 | P1 | P2 | A1 | A2 | C1 |
|---|---|---|---|---|---|---|---|
| Jacket Temperature ° C. | 95 | 30 | — | — | 95 | 0 | 30 |
| Product Exit Temperature ° C. | — | — | 56.3 | — | 91.8 | 18.7 | — |
| Rotor Speed r.p.m | <60 | <60 | — | — | 1000 | 4000 | 2000 |
| % Pump Stroke | — | — | 70 | 99 | — | — | — |

EXAMPLE 12

Foaming Cleanser

Figure 4:
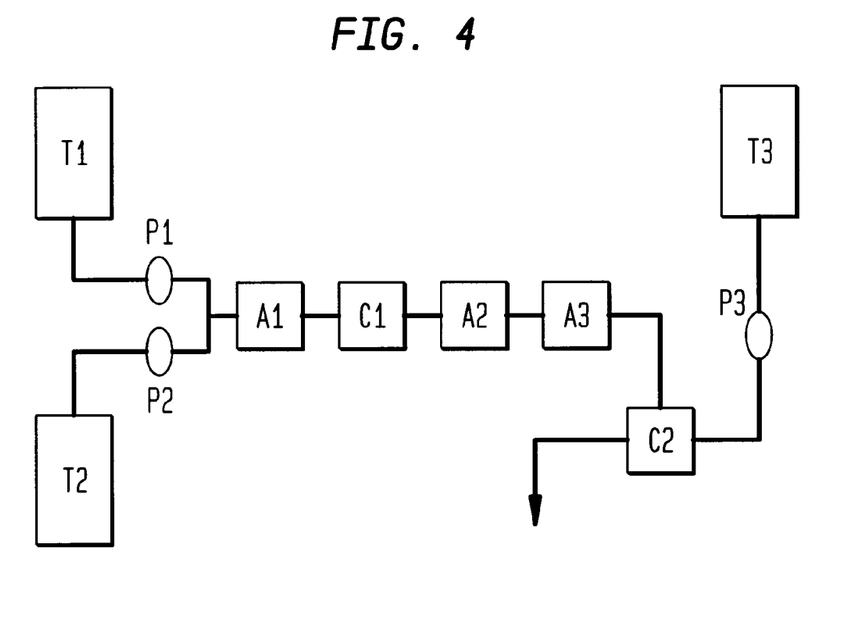

This preparation was carried out using a micro-votator line as shown by FIG. 4. Gellan (Kelcogel F, Kelco) was dissolved in hot de-ionised water (>90° C.) using a Silverson mixer and transferred to a jacketed stirred tank T1 and maintained at 90° C. with slow stirring (solution M). A solution of calcium chloride was made in de-ionised water and transferred to a second stirred tank T2. The surfactant mixture N of Example 4 was prepared and transferred to a third stirred tank T3. The micro-votator line had the two feed tanks T1,T2 connected via separate channels P1,P2 of a proportioning pump to a Teepiece located at the inlet to a first scraped-surface heat exchanger A1 which was followed in sequence by a mixer C1 and two further heat exchangers A2, A3. Finally, the outlet of the last heat exchanger A3 was connected to a centrally located port of a second mixer C2 which was supplied from feed tank T3 via a third proportioning pump channel P3.

The three solutions (M, N and $CaCl_2$) were processed through this line to form a stable, pourable product containing 16% surfactant which foamed well in use. The compositions and the process conditions are set out in the following two tables:

COMPOSITIONS - EXAMPLE 12

| Material | Solution M (% w/w) | $CaCl_2$ Solution (% w/w) | Solution N (% w/w) | Product Composition (% w/w) |
|---|---|---|---|---|
| Gellan | 1.875 | — | — | 0.80 |
| Calcium chloride $2H_2O$ | — | 2.7 | — | 0.50 |
| SLES (pure) | — | — | 43.28 | 8.67 |
| CAPB (100% active) | — | — | 6.68 | 1.33 |
| Propylene glycol | — | — | 14.55 | 9.90 |
| De-ionised water | 98.13 | 97.30 | 50.04 | 88.70 |

PROCESS CONDITIONS - EXAMPLE 12

| | Jacket Temperature (° C.) | Product Exit Temperature (° C.) | Rotor Speed (r.p.m) | % Pump Stroke |
|---|---|---|---|---|
| T1 | 90 | 83 | <60 | — |
| T2 | 90 | — | — | — |
| T3 | 30 | — | — | — |
| P1 | — | — | — | 80 |
| P2 | — | — | — | 20 |
| P3 | — | — | — | 47 |
| A1 | −15 | 15 | 2500 | — |
| C1 | 0 | — | 2000 | — |
| A2 | 0 | 6.5 | 1000 | — |
| A3 | 0 | 3 | 1000 | — |
| C2 | 5 | — | 1000 | — |

EXAMPLE 13–26

Foaming Cleansers

The following compositions were prepared using a water jacket surrounded wall scraping vessel similar to that described in relation to example 1, optionally under vacuum if necessary, in particular where the composition being processed is relatively thick (e.g. has a relatively high agar concentration), or it is particularly required to avoid aeration. The processing conditions were those generally described in relation to example 11, where the agar, water and polyols (eg. glycerol, PEG 400, propan-1,2 diol) and ethanol were prepared as a presolution, being mixed using a Silverson stirrer before being transferred to a jacketed tank T1 and being maintained at 95° C. The remainder of the components, except the perfume and preservative, are then formulated with the surfactants and processed as described in relation to example 11.

| | Example (% w/w) | | | | | |
|---|---|---|---|---|---|---|
| Material | 13 | 14 | 15 | 16 | 17 | 18 |
| Agar (Luxara 1253) | 0.3 | 0.3 | 0.3 | 0.1 | 0.3 | 1.3 |
| Cocoyl Sarcosinic acid | 3.7 | 3.7 | 3.7 | — | — | — |
| N-cocoyl DL-Alanic acid | 3.8 | 3.8 | 3.8 | — | 3.5 | — |
| Lauric acid | 6.6 | 6.6 | 6.6 | 8.8 | 10.0 | — |
| Cocoamide monoethanolamine | 1.9 | 1.9 | 1.9 | 2.5 | — | — |
| Triethonolamine | 5.0 | 5.0 | 5.0 | — | 13.4 | 6.7 |
| PEO(150) PPO (30) poloxamer | 10.0 | 10.0 | 10.0 | 10.0 | 10.0 | — |
| Glycerol | 14.0 | 14.0 | 14.0 | 14.0 | 14.0 | 54.0 |
| PEG 400 | 14.0 | 14.0 | 14.0 | 14.0 | 14.0 | 3.5 |
| 1 mm mineral oil capsules | 1.0 | — | — | 1.0 | 1.0 | — |
| 10–25 $\mu$m polyester fibres | — | 1.0 | — | — | — | — |
| Opacified ($TiO_2$) agarchop gel | — | — | 1.0 | — | — | — |
| Perfume | 0.1 | 0.1 | 0.1 | 0.1 | 0.1 | 0.1 |
| Kathan CG | 0.05 | 0.05 | 0.05 | 0.05 | 0.05 | 0.04 |
| Potassium cocoyl glycinate | — | — | — | 8.8 | — | — |
| Potassium hydroxide | — | — | — | 4.9 | — | — |
| $C_9$–$C_{15}$ mono/di alkyl phosphoric acid | — | — | — | — | 7.0 | — |
| Cocoyl glutamic acid | — | — | — | — | — | 11.8 |
| Myristyl glutamic acid | — | — | — | — | — | 4.0 |
| POE sorbitan triisostearate | — | — | — | — | — | 1.4 |
| Water | To 100 | To 100 | To 100 | To 100 | To 100 | To 100 |

| | Example (% w/w) | | | | | | | |
|---|---|---|---|---|---|---|---|---|
| Material | 19 | 20 | 21 | 22 | 23 | 24 | 25 | 26 |
| Agar (Luxara 1253) | 4.5 | 1.0 | 1.0 | 3.0 | 3.0 | 2.0 | 1.3 | 2.0 |
| Potassium cocoyl glycinate | 16.0 | 18.0 | 6.0 | — | — | 16.0 | 11.7 | 18.0 |
| Glycerol | 16.0 | 50.0 | 90.0 | — | 14.0 | — | 9.1 | — |
| PEG 400 | 16.0 | — | — | — | 14.0 | — | 9.1 | — |
| Perfume | 0.1 | 0.1 | — | 0.1 | — | — | — | — |
| Kathan CG | 0.05 | 0.05 | 0.05 | 0.05 | 0.05 | 0.05 | 0.05 | 0.05 |
| 1 mm mineral oil microcapsules | — | 0.4 | — | — | — | — | — | — |
| $C_9$–$C_{15}$ mono/dialkyl phosphoric acid | — | — | — | 12.4 | 12.4 | — | — | — |
| $C_{12}$/$C_{14}$ alkyl (4EO mono Alkyl ether citrate | — | — | — | 2.6 | — | — | — | — |
| Potassium hydroxide | — | — | — | 6.0 | 6.0 | — | — | — |
| Propan-1,2 diol | — | — | — | 28.0 | — | — | — | — |
| Lauryl (10EO) ether carboxylic acid | — | — | — | — | 2.9 | — | — | — |
| Precipitated silica | — | — | — | — | 3.0 | — | — | — |
| Phoenix 3000 opt FW | — | — | — | — | — | — | 0.1 | 0.1 |
| Ethanol | — | — | — | — | — | — | 35.0 | 35.0 |
| Neosorb 70/70 (70% sorbitol solution) | — | — | — | — | — | To 100 | — | — |
| Water | To 100 | To 100 | To 100 | To 100 | To 100 | — | To 100 | To 100 |

In compositions 25 and 26, ethanol was posted added to the shear gel.

In certain embodiments including relatively high (e.g greater than about 5%, possibly greater than about 20%) of short chain monohydric alcohols such as ethanol, it is possible to manufacture the shear gel in the presence of the alcohol without the surfactant, and then subsequently post-dosing the surfactant to provide the final composition. This provides a way of manufacturing compositions containing relatively high levels of short chain monohydric alcohols, which compositions may otherwise be relatively difficult to make.

Various benefits were found to be associated with aspects of the above compositions. For example, the compositions which contained potassium cocoyl glycinate were found to have good clarity and be very shear thinning suitable for direct application to eg. the face. Also, various of the compositions were found to have the surfactant in isotropic solution in a temperature range of 5–45° C., in which case the viscosity of the product is governed solely by the shear gel particles. In those instances, the viscosity is relatively unaffected by temperature, which facilitates the packaging of the product, making it for example suitable for distribution in tubes.

Also, compositions comprising relatively substantial levels of polyols are found to be tolerant of the coextrusion or injection into them of surfactant during manufacturing, and certainly more so than systems which were structured by eg. clay or Carbopol(). It was also found that the incorporation of polyols tended to affect the gelation rate and mechanism, with the result that a relatively mild shearing regime could be used to generate the shear gels, and preventing the formation of hard gel clumps in unsheared parts of the mixer on cooling. Compositions containing the polyols also tended to suffer reduced levels of syneresis

EXAMPLES 27–32

The following additional face wash compositions were prepared.

In the manufacturing method a thermostatically controlled wall heater vessel was used, together with a wall scraping paddle. The vessel was evacuated to prevent air entrapment.

Into the vessel was charged water, polyol and agar to provide a pre-solution. This mixture was heated with stirring to 90° C. The resulting solution was then cooled to 50° C. with rapid paddle mixing. The mixture was then further cooled to 25° C. with slow cooling, and rapid paddle mixing, in order to form the shear gel. Into the shear gel was added the solid surfactant, which was dissolved by warming the composition to 40° C. and gently mixing.

The composition was then cooled, any perfume, preservatives and whitening agent were added, and the composition discharged.

The compositions contain relatively high levels of polyol materials.

| Component | Example 27 | Example 28 | Example 29 | Example 30 | Example 31 | Example 32 |
|---|---|---|---|---|---|---|
| Water | 38 | 38 | 28 | 32.8 | 28 | 28 |
| Glycerol | 40 | 40 | 40 | 40 | 40 | 40 |
| Agar | 2 | 2 | 2 | 2 | 2 | 2 |
| Potassium Cocoglutamate | 20 | 19.8 | 20 | 18 | 17.8 | 17.8 |
| PEG 400 | — | — | 10 | 5 | — | 10 |
| Perfume | — | 0.15 | — | 0.15 | 0.15 | 0.15 |
| Preservative | — | 0.05 | — | 0.05 | 0.05 | 0.05 |
| Whitener | — | — | — | 2 | 2 | 2 |
| PEG 1500 | — | — | — | — | 10 | — |

Examples 33 40 represent further suitable compositions according to the invention.

| Material | 33 | 39 | 35 | 36 | 37 | 38 | 39 | 40 |
|---|---|---|---|---|---|---|---|---|
| Agar | 3.2 | 3.2 | 3.2 | 3.2 | | | | 3.2 |
| Iota Carageenan | | | | | 1.2 | 1.2 | 1.2 | |
| Kappa Carageenan | | | | | 0.8 | 0.8 | 0.8 | |
| SLES (as 100%) | 10 | 10 | 10 | | 8 | 3 | 6 | 10 |
| CAPB (as 100%) | 3 | 3 | 5 | 2 | 2 | 5 | | 4 |
| Sodium lauryl isethionate | | 2 | | 3 | | 3 | 2 | 2 |
| Lauryl amphoatcetate | | | 3 | 2 | | | | 3 |
| Potassium laurate | | | | | 12 | | | |
| Potassium myristate | | | | | | 6 | | |
| Jaguar 13 S | | 0.5 | 1.2 | 0.7 | 0.4 | 0.3 | | 0.8 |
| Petrolatum | | 13 | | | | | | |
| Sunflower seed oil | | | | | | | 10 | 20 |
| Polydimethylsiloxane | 5 | 5 | | | | | | 3 |
| Glycerol | 3 | 22 | | 5 | | | | |
| Parsol MCX | | | | 6 | | 3 | | |
| Parsol 1789 | | | | 2 | | 1 | | |
| Water to 100% | | | | | | | | |

What is claimed is:

1. An aqueous detergent composition, which is in the form of a thickened, mobile fluid, shear gel comprising:

(a) a foaming detergent, wherein said detergent comprises a surfactant selected from the group consisting of anionic surfactants, amphoteric surfactants and zwitterionic surfactants and wherein at least 3% by wt. of said composition comprises anionic surfactant;

(b) 5% to 90% by weight of a polyol material selected from the group consisting of glycerol; sorbitol; hexandiol; propan-1,2 diol; 1,3 butylene glycol; propylene glycol; hexylene glycol; and polyethylene glycols and polypropylene glycols having molecular weights in the range 100 to 4,000; and (c) 0.1 to 10% by weight of a polymer or polymer mixture which is capable of forming a reversible gel, wherein said polymer or polymer mixture is selected such that said polymer or polymer mixture is dissolved above its gel point and becomes mobile, and said polymer or mixture is then cooled below its gel point and under shear such that the polymer is present in the composition as a multiplicity of individual gel particles having a particle size of less than 200 micrometers; wherein said polymer or polymer mixture includes a polysaccharide chain of natural origin.

2. A composition according to claim 1 containing 5 to 25 wt % anionic surfactant.

3. A composition according to claim 1 wherein the foaming detergent contains a nonionic surfactant selected from the group consisting of alkyl glycosides, O-alkanoyl glycosides, polyethylene oxide-polypropylene oxide block copolymers, alkyl polyhydroxyamides, alkyl aldobionamides and mixtures thereof.

4. A composition according to claim 1 wherein the polymer or polymer mixture comprises kappa carrageenan.

5. A composition according to claim 1 wherein the polymer or polymer mixture comprises agar.

6. A composition according to claim 1 including suspended particles of a liquid or solid other than the polymer or polymer mixture gel.

7. A composition according to claim 6, wherein the suspended phase is selected from the group consisting of silicone oils or gums, triglyceride oils or waxes, mineral oil, petrolatum, polyethylene and mixtures thereof.

8. A composition according to claim 6 wherein the suspended particle is a sunscreen.

9. A method of preparing a detergent composition according to claim 1 which comprises forming a hot, mobile aqueous solution of the polymer or polymer mixture cooling the solution through its gel temperature while subjecting it to shear, and incorporating foam-forming detergent before or after cooling.

10. A method according to claim 9 wherein the surfactant is added to the solution after cooling to 35° C. or less.

11. A method according to claim 10 wherein the polymer or polymer mixture comprises kappa carrageenan and the surfactant is present in the aqueous solution while it is cooled under shear.

* * * * *